US011479568B2

(12) United States Patent
Arkles et al.

(10) Patent No.: US 11,479,568 B2
(45) Date of Patent: Oct. 25, 2022

(54) SILACROWN ETHERS, PHARMACEUTICAL COMPOSITIONS THEREOF, AND THERAPEUTIC APPLICATIONS THEREOF

(71) Applicants: Barry C. Arkles, Pipersville, PA (US); Jeffrey S. Arkles, Lafayette Hill, PA (US)

(72) Inventors: Barry C. Arkles, Pipersville, PA (US); Jeffrey S. Arkles, Lafayette Hill, PA (US)

( * ) Notice: Subject to any disclaimer, the term of this patent is extended or adjusted under 35 U.S.C. 154(b) by 0 days.

(21) Appl. No.: 17/464,301

(22) Filed: Sep. 1, 2021

(65) Prior Publication Data

US 2022/0073543 A1    Mar. 10, 2022

Related U.S. Application Data

(60) Provisional application No. 63/075,517, filed on Sep. 8, 2020.

(51) Int. Cl.
*C07F 7/18* (2006.01)
*A61P 9/00* (2006.01)

(52) U.S. Cl.
CPC ............. *C07F 7/1804* (2013.01); *A61P 9/00* (2018.01)

(58) Field of Classification Search
CPC ................................ C07F 7/1804; A61P 9/00
USPC ........................................................ 549/214
See application file for complete search history.

(56) References Cited

U.S. PATENT DOCUMENTS 4,927,952 A    5/1990    Gueyne et al.

FOREIGN PATENT DOCUMENTS

CA         1240442 A       8/1988
WO      2020082026 A1     4/2020

OTHER PUBLICATIONS

Liptuga et al., Silicon-containing crown ether, Zhurnal Obschchei Khimii, vol. 48, No. 5, pp. 1185-1186 (1978) (Abstract only).
Paulusse et al., "Free Radical Polymers with Tunable and Selective Bio- and Chemical Degradability," Journal of American Chemical Society, vol. 131, pp. 9805-9812 (2009).
International Search Report and Written Opinion dated Jan. 3, 2022 in International Application No. PCT/US2021/048327.
Antoszczak et al., "Anti-parasitic activity of polyether ionophores," European Journal of Medicinal Chemistry, vol. 166, pp. 32-47 (2019).
Arkles et al., "Silacrowns: Phase-Transfer Catalysts," Organometallics, vol. 2, pp. 454-457 (1983).
Benjamin et al., "Heart Disease and Stroke Statistics—2019 Update," Circulation, vol. 139, pp. e56-e528 (2019).
Benziger et al., "The Global Burden of Disease Study and the Preventable Burden of NCD," Global Heart, vol. 11, No. 4, pp. 393-397 (2016).
Chehardoli et al., "The role of crown ethers in drug delivery," Supramolecular Chemistry, vol. 31, No. 4, pp. 221-238 (2019).
Davignon et al., "Role of Endothelial Dysfunction in Atherosclerosis," Circulation, vol. 109, Suppl. III, pp. III-27-III-32 (2004).

(Continued)

*Primary Examiner* — Taylor V Oh
(74) *Attorney, Agent, or Firm* — Panitch Schwarze Belisario & Nadel LLP (57) ABSTRACT

Large ring silacrown ethers having at least fourteen ring atoms with at least one lipophilic or hydrophobic substituent on the ring and/or on the silicon atom are provided. Pharmaceutical compositions containing these silacrown ethers and the use of these materials as therapeutic agents are also described.

22 Claims, 2 Drawing Sheets

Vascular tissue contractile response as a function of crown and silacrown ether concentration (56) References Cited

OTHER PUBLICATIONS

Deng et al., "Application of the Nano-Drug Delivery System in Treatment of Cardiovascular Diseases," Frontiers in Bioengineering and Biotechnology, vol. 7, No. 489, pp. 1-18 (2020).
Flögel et al., "In Vivo Monitoring of Inflammation After Cardiac and Cerebral Ischemia by Fluorine Magnetic Resonance Imaging," Circulation, vol. 118, pp. 140-148 (2008).
Gad et al., "Thirteen Cationic Ionophores: Their Acute Toxicity, Neurobehavioral and Membrane Effects," Drug and Chemical Toxicology, vol. 8, No. 6, pp. 451-468 (1985).
Giles et al., "Impaired Vasodilation in the Pathogenesis of Hypertension: Focus on Nitric Oxide, Endothelial-Derived Hyperpolarizing Factors, and Prostaglandins," The Journal of Clinical Hypertension, vol. 14, No. 4, pp. 198-205 (2012).
Kevin et al., "Polyether ionophores: broad-spectrum and promising biologically active molecules for the control of drug-resistant bacteria and parasites," Expert Opinion Drug Discov., vol. 4, No. 2, pp. 109-146 (2009).
Kowey, P. R., "Pharmacological Effects of Antiarrhythmic Drugs," Arch. Intern. Med., vol. 158, pp. 325-332 (1998).
Kubo et al., "Endothelium-Dependent Vasodilation is Attenuated in Patients with Heart Failure," Circulation, vol. 84, No. 4, pp. 1589-1596 (1991).
Kutova et al., "Targeted Delivery to Tumors: Multidirectional Strategies to Improve Treatment Efficiency," Cancers, vol. 11, No. 68, pp. 1-33 (2019).
McMurray et al., "Angiotensin-Neprilysin Inhibition versus Enalapril in Heart Failure," The New England Journal of Medicine, vol. 371, No. 11, pp. 993-1004 (2014).
Miyasaka et al., "Secular Trends in Incidence of Atrial Fibrillation in Olmsted County, Minnesota, 1980 to 2000, and Implications on the Projections for Future Prevalence," Circulation, vol. 114, pp. 119-125 (2006).
Pannell et al., "Concerning the Relative Non-Toxicity of Silacrown Ionophores," Pharmacology Biochemistry & Behavior, vol. 21, Suppl. 1, pp. 77-80 (1984).
Pannell et al., "Silacrown Ionophores," Journal of Membrane Science, vol. 32, pp. 83-91 (1987).
Rich, S., "The Effects of Vasodilators in Pulmonary Hypertension: Pulmonary Vascular or Peripheral Vascular?," Circulation: Heart Failure, vol. 2, No. 2, pp. 145-150 (2009).
Ritch et al., "Silicon Analogues of Crown Ethers and Cryptands: A New Chapter in Host-Guest Chemistry," Angew. Chem. Int. Ed. vol. 46, pp. 4610-4613 (2007).
Senapati et al., "Controlled drug delivery vehicles for cancer treatment and their performance," Signal Transduction and Targeted Therapy, vol. 3, No. 7, pp. 1-19 (2018).
Supek et al., "Could LogP be a principal determinant of biological activity in 18-crown-6 ethers? Synthesis of biologically active adamantane-substituted diaza-crowns," European Journal of Medicinal Chemistry, vol. 46, No. 8, 31 pages (2011).
Taylor et al., "Combination of Isosorbide Dinitrate and Hydralazine in Blacks with Heart Failure," The New England Journal of Medicine, vol. 351, No. 20, pp. 2049-2057 (2004).
Rosenfeld et al., "Calcium-activated potassium channels and nitric oxide coregulate estrogen-induced vasodilation," Am. J. Physiol. Heart Circ. Physiol., vol. 279, pp. H319-H328 (2000).

Fig. 1

Vascular tissue contractile response as a function of crown and silacrown ether concentration

Fig. 2

Vascular tissue contractile response as a function of crown ether concentration

SILACROWN ETHERS, PHARMACEUTICAL COMPOSITIONS THEREOF, AND THERAPEUTIC APPLICATIONS THEREOF

CROSS-REFERENCE TO RELATED APPLICATION

This application claims priority to U.S. Provisional Application No. 63/075,517, filed Sep. 8, 2020, the disclosure of which is herein incorporated by reference.

BACKGROUND OF THE INVENTION

Cardiovascular disease (CVD) is a leading cause of morbidity and mortality globally. Despite existing therapeutics, 17.8 million global deaths were attributed to CVD in 2017, with an even larger impact on morbidity and quality of life (E. J. Benjamin et al., *Circulation*, vol. 139, no. 10, pp. e56-e528 (2019)). Vascular function and dysfunction contribute to the pathophysiology of many forms of CVD. Increased vascular resistance mediated through multiple mechanisms including the renin angiotensin aldosterone system and endothelial dysfunction play a critical role in the pathophysiology of CVD. Systemic (HTN) and pulmonary hypertension (PAH), atherosclerosis (ATH), and congestive heart failure (CHF) are forms of CVD in which vascular resistance plays a critical role in the disease process. The current therapies to treat these diseases mostly target vasodilation to lower vascular resistance. In the case of CHF, loss of endothelial vasodilation is an adaptation to abnormal cardiac function (S. H. Kubo, et al., *Circulation*, vol. 84, no. 4, pp. 1589-1596 (1991)). This vasoconstriction in turns worsens cardiac function. Importantly, vasodilatory medications have been associated with marked improvements in quality of life, morbidity and mortality (see A. L. Taylor et al., *N. Engl. J. Med.*, vol. 351, no. 20, pp. 2049-2057 (2004); J. J. V. McMurray et al., *N. Engl. J. Med.*, vol. 371, no. 11, pp. 993-1004 (2014)).

HTN and PAH are diseases which are inherently related to altered vascular resistance. It is important to note that different vascular beds have different mechanisms of vasodilation. Accordingly, drugs currently used to treat HTN and PAH are distinct and rely on separate mechanisms (see S. Rich, *Circ. Heart Fail.*, vol. 2, no. 2, pp. 145-50 (2009) and T. D. Giles et al., *J. Clin. Hypertens.*, vol. 14, no. 4, pp. 198-205 (2012)).

ATH can cause disruption of the arterial wall, leading to limited blood flow manifested as heart attack, stroke, or peripheral arterial disease. While ATH is a complex disease, abnormal endothelial function and vasoconstriction are notable facets (J. Davignon et al., *Circulation*, vol. 109, pp. III-27-III-32 (2004)).

Another form of CVD is abnormal heart rhythms. Arrhythmias range from minimally symptomatic to immediately fatal. Cardiac arrhythmias, such as atrial fibrillation, are common, affecting millions (Y. Miyasaka et al., *Circulation*, vol. 114, no. 2, pp. 119-125 (2006)). Other arrhythmias, such as ventricular tachycardia and ventricular fibrillation, are less common but are associated with severe outcomes, such as syncope and sudden death. Fundamentally, normal cardiac rhythm relies on maintaining ion flux across the cell membrane. Cardiac myocytes are highly evolved to regulate ionic flux, minimizing the risk of these potentially fatal arrhythmias. However, in disease states, abnormal membrane potentials are associated with arrhythmia development. Drugs targeting specific ion channels (e.g., sodium, potassium and calcium) are commonly used to treat these arrhythmias (P. R. Kowey, *Archives of Internal Medicine*, vol. 158, no. 4. American Medical Association, pp. 325-332 (1998).

Myocardial infarction (MI) is one of the leading causes of morbidity and mortality. Drugs used to treat a number of cardiac diseases have systemic side effects which limit their therapeutic use. Therefore, there is a significant research interest in targeted therapeutics for CVD (Y. Deng et al., *Frontiers in Bioengineering and Biotechnology*, vol. 7. Frontiers Media S.A., p. 489 (2020)). One example is ATH, which plays a critical role in myocardial infarction and stroke and is largely mediated by inflammation. Research has shown that nanoparticles accumulate at sites of inflammation (U. Flogel et al., *Circulation*, vol. 118, no. 2, pp. 140-148 (2008), providing a potential therapeutic target for treating ATH.

The potential therapeutic use of ion-channeling drugs is not limited to CVD. Ionophores and related compounds have shown promise in treating a broad range of bacteria and parasites (see D. A. Kevin et al., *Expert Opinion on Drug Discovery*, vol. 4, no. 2, pp. 109-146 (2009)).

For example, ion-channeling pharmaceuticals such as valinomycin, shown below, is a large (36-atom ring) macrocyclic polypeptide that has shown potential as a therapeutic agent for Covid-19 and under physiological conditions can be degraded by a variety of in vivo processes.

valinomycin

Chemotherapy is often limited by systemic side effects. Malignant cells are known to develop resistance to chemotherapeutic drugs and other adaptations which make chemotherapy less effective. (O. M. Kutova et al. *Cancers*, vol. 11, no. 68; pp. 1-33 (2019)). Therefore, chemotherapeutic sensitizing agents which overcome resistance by altering cellular permeability may be particularly useful[JA1]. Currently, however, ionophores are limited because of their systemic toxicities.

Crown Ethers

Crown ethers are cyclic ether compounds consisting of oxygen atoms each separated by two carbon atoms, which may also be described as cyclic oligomers of ethylene oxide with repeat unit —$CH_2CH_2O$—. Crown ethers are named as "X-crown-Y," where X is the total number of atoms in the ring and Y is the total number of oxygen atoms. Silacrown ethers contain a silicon atom in the ring between two oxygen atoms, replacing one "CH$_2$CH$_2$" unit.

Previously reported silacrown ethers are relatively simple structures, as shown below. In contrast to conventional crown ethers, the Si—O—C bond is not hydrolytically stable, which provides a mechanism for degradation (See K. H. Pannell, et al. *Pharm. Biochem. Behav.*, 21, Supp. 1, pp. 77-80 (1984)).

Crown ethers are notable for their ability to complex alkali and alkaline earth metal ions and to effect their transport across both liquid and real membranes. In many physiological responses, alkali metal ion-transport is modulated by alkaline earth metals, such as Ca$^{+2}$ modulation of K$^+$ (see Rosenfeld et al; *Am J Physiol Heart Circ Physiol* 279, H319-H328, (2000)). This property has raised considerable interest in their potential to mimic the naturally occurring ionophores, and the unique structure of crown ethers shows promise for targeted drug delivery (Chehardoli et al., *Supramolecular Chemistry*, vol. 31, no. 4., pp. 221-238 (2019)).

Initial screening studies on vascular smooth muscle response to specific crown ethers and their derivatives (mainly the dicyclohexyl derivatives) may be of therapeutic value due to the vasodilating properties. This is the result of the bifunctional structure of the ionophore permitting metal ion binding of small ions to the hydrophilic interior and an external hydrophobic region that permits solubilization of the resulting complexes in a lipid environment. The selectivity of these crown ethers has been shown to effectively transport metal ions across lipid membranes, often with high selectivity, and many of the factors that alter this ability are now well established. Thus, ionophore substituents altering basicity, flexibility, strength of metal binding, counter-ion character for neutral ionophore carriers, and temperature effects have all been established beyond the very basic and crucial macrocycle cavity size feature.

Because of the potential therapeutic application of this class of compounds, studies have been reported concerning their physiological properties. This has resulted in the discovery that some of the synthetic compounds are active upon the central nervous system and can produce such effects upon mice and rabbits as tremors, weakness, and certain reflex degradation (S. C. Gad et al., "Thirteen Cationic Ionophores: Their Acute Toxicity, Neurobehavioral and Membrane Effects," *Drug and Chemical Toxicology*, 8:6, 451-468 (1985). In the case of rats, testicular atrophy has been observed. Effects upon the central nervous system seem to be readily reversible upon removal of the ionophores. Even with constant dose levels the effects decrease after a short period of time.

Crown type ionophores offer the potential for use as anti-hypertensive and vasodilator drugs. Availability studies are limited, and no systematic structure/function studies are reported. The systemic effects of these materials arise, in part, due to their persistence in vivo without readily accessible biological pathways for degradation and elimination.

The ability of crown ethers to affect and alter the permeability of the cell membrane makes them inherently interesting therapeutic choices for potential treatment of cardiac arrhythmias. The structure of the crown ether could be altered to allow for selective permeability of important ions thereby making them antiarrhythmic agents. However, the use of crown ethers poses challenges due to their persistence in vivo and associated systemic toxicology.

Silacrown ethers are also anticipated to have many potential therapeutic effects related to CVD, but with shorter persistence in vivo. While silacrown ethers with relatively simple structures, that is, those having relatively low numbers of ring atoms and low potential for solubility in lipids have been considered in the past, these compounds are not structurally consistent with the requirements of cellular membrane incorporation to provide relevant ion-channeling. Accordingly, there remains a need in the art for silacrown ethers which address some of the shortcomings of known compounds for therapeutic applications.

BRIEF SUMMARY OF THE INVENTION

In one aspect of the disclosure, provided is a silacrown ether comprising at least fourteen ring atoms, one methyl group on the silicon atom, and at least one lipophilic or hydrophobic substituent on the silicon atom and/or on the ring, provided that if the at least one lipophilic or hydrophobic substituent is a methyl group on the silicon atom, the silacrown ether further comprises at least one lipophilic or hydrophobic substituent on the ring.

In another aspect of the disclosure, provided is a silacrown ether comprising at least seventeen ring atoms, at least one methyl group on the silicon atom, and at least one lipophilic or hydrophobic substituent on the silicon atom and/or on the ring.

In another aspect, provided is a therapeutic agent comprising a silacrown ether as described herein.

In another aspect, provided is a pharmaceutical composition comprising a silacrown ether as described herein and a pharmaceutically acceptable carrier.

In yet another aspect, provided is a method of treating a disease selected from cardiovascular disease, cancer, a bacterial infection, and a parasite, the method comprising administering a silacrown ether or a pharmaceutical composition as described herein to a subject in need thereof.

BRIEF DESCRIPTION OF THE SEVERAL VIEWS OF THE DRAWINGS

The following detailed description of preferred embodiments of the present invention will be better understood when read in conjunction with the appended drawing. For the purposes of illustrating the invention, there is shown in the drawing which is among the preferred embodiments. It is understood, however, that the invention is not limited to the precise arrangements and instrumentalities shown. In the drawings.

DETAILED DESCRIPTION OF THE INVENTION

The disclosure relates to large ring silacrown ethers having at least fourteen ring atoms, one methyl group on the silicon atom, and at least one lipophilic or hydrophobic substituent on the silicon atom and/or on the ring, pharmaceutical compositions thereof, and their use as therapeutic agents. If the at least one lipophilic or hydrophobic substituent is a methyl group on the silicon atom, the silacrown ether further comprises at least one lipophilic or hydrophilic substituent on the ring.

The disclosure also relates to large ring silacrown ethers comprising at least seventeen ring atoms, at least one methyl group on the silicon atom, and at least one lipophilic or hydrophobic substituent on the silicon atom and/or on the ring, pharmaceutical compositions thereof, and their use as therapeutic agents.

The term "lipophilic" refers to the ability to dissolve in fats, oils, lipids, and non-polar solvents. "Hydrophobic" refers to a physical property of seemingly being repelled from water, more correctly, not attracted to water; hydrophobic molecules tend to be non-polar. While the terms lipophilic and hydrophobic are often used interchangeably, they are not synonymous; silicones and fluorocarbons, as well as methyl substituents, are hydrophobic but not lipophilic, and lipid bilayers are generally considered to be hydrophobic.

Exemplary lipophilic and hydrophobic substituents include, but are not limited to, substituted and unsubstituted linear, branched, and cyclic alkyl groups having one to about twenty-four carbon atoms, such as, without limitation, methyl (which is hydrophobic but not lipophilic), octyl, isopropyl, and cyclohexyl groups, as well as hydrophobic aromatic groups such as substituted and unsubstituted phenyl groups. These lipophilic and hydrophobic substituents bonded to the silicon atom are depicted R in the exemplary structures below; cyclohexyl groups bonded to the ring are also shown. The silacrown ethers may additionally contain a lipophilic or hydrophobic substituent as described above bonded directly to the ring, such as the preferred cyclohexyl group shown below; other substituents may alternatively or additionally be bonded directly to the ring, such as hydrophilic aromatic groups (e.g., benzene), polyalkyl ethers (e.g., methoxy(diethyleneoxy)propyl), and amidic groups (e.g., acetamidopropyl).

Preferred embodiments of the disclosure include silacrown eithers containing at least one cyclohexane group on the ring and those containing at least one benzene group on the ring.

Two general silacrown ethers according to embodiments of the disclosure have formulas (1) and (2) below, in which n is an integer of at least 3. Thus, the compound having formula (1) has at least fourteen ring atoms and the compound having formula (2) has at least twenty-three ring atoms.

(1)

(2)

Several exemplary silacrown ethers according to the disclosure are shown below.

Sila-Dicyclohexano-23-Crown-8

Sila-Cyclohexano-23-Crown-8

Sila-Dicyclohexano-14-Crown 5

Methylalkylsila-17-Crown-6

When R in the structures above is a methyl group, the resulting compounds are dimethylsila-dicyclohexano-23-crown-8, dimethylsila-cyclohexano-23-crown-8, dimethylsila-dicyclohexano-14-crown-5 and dimethylsila-17-crown-6.

Other smaller ring homologs are also within the scope of the disclosure, such as cyclohexylmethylsila-17-crown-6 and cyclohexylmethylsila-20-crown-7, shown below.

Other silacrown structures analogous to conventional crown ethers are also within the scope of the disclosure, such as dimethylsila-dibenzo-17-crown-6, shown below, which is analogous to dibenzo-18-crown-6.

The structures shown and described above are exemplary, not limiting, and alternative compounds within the scope of the disclosure are silacrown ethers with adjustable ring-size, hydrophobic character and susceptibility to hydrolysis.

Methods of Preparation

The compounds described herein may be prepared by directed esterification using a base acceptor or transesterification, as shown in Schemes 1 and 2 below, where TEA is triethylamine.

Scheme 1 Synthesis of dimethylsila-14-cyclohexylcrown-5

Scheme 2 Synthesis of cyclohexylmethylsila-14-crown-5

Pharmaceutical Compositions and Therapeutic Agents

In other embodiments, the disclosure relates to a therapeutic agent or pharmaceutical composition containing an effective amount of a silacrown ether having at least fourteen ring atoms, one methyl group on the silicon atom, and at least one lipophilic or hydrophobic substituent on the silicon atom and/or on the ring, provided that if the at least one lipophilic or hydrophobic substituent is a methyl group on the silicon atom, the silacrown ether further comprises at least one lipophilic or hydrophilic substituent on the ring, and optionally a pharmaceutically acceptable carrier. Appropriate hydrophobic substituents are as previously described.

In other embodiments, the disclosure relates to a therapeutic agent or pharmaceutical composition containing an effective amount of a silacrown ether comprising at least seventeen ring atoms, at least one methyl group on the silicon atom, and at least one lipophilic or hydrophobic substituent on the silicon atom and/or on the ring, and optionally a pharmaceutically acceptable carrier.

A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For solid oral preparations, for example, powders, capsules, caplets, gelcaps, and tablets, suitable carriers and additives include starches, sugars, diluents, granulating agents, lubricants, binders, disintegrating agents and the like.

Compositions can be formulated in any matter suitable for administration to a subject to facilitate administration and improve efficacy, including, but not limited to, oral (enteral) administration and parenteral injections, preferably for oral administration. Compositions suitable for oral administration include tablets, capsules, etc.

In yet another aspect, provided is a method of preparing a pharmaceutical composition comprising combining a silacrown ether as described herein with at least one pharmaceutically acceptable carrier. Pharmaceutical compositions can be prepared by any method known in the art in view of the present disclosure, and one of ordinary skill in the art will be familiar with such techniques used to prepare pharmaceutical compositions, such as by conventional pharmaceutical compounding techniques, including but not limited to, conventional admixing, dissolving, granulating, emulsifying, encapsulating, entrapping or lyophilizing processes.

Methods of Use

It has been found that the silacrown ethers are effective as therapeutic agents, and the ability to adjust variables such as ring size, hydrophobic character, and susceptibility to hydrolysis is critical in selecting potential structures for use as therapeutic agents.

As an illustrative example, the lipophilic/hydrophilic balance of dicyclohexano-18-crown-6 and cavity size should approach the threshold of activity for natural macrocycles such as valinomycin, but the toxicity is anticipated to be too great for consideration in most therapeutic applications. However, the silacrown ethers described herein have either been shown or anticipated to exhibit reduced toxicity relative to the known crown compounds.

The ability to provide adjustable molecular structures with the ability to match to the requirements of membrane incorporation as well as in vivo persistence is provided by the silacrown ethers described herein which contain hydrophobic substitution. By way of general example, two approaches to altering the incorporation into cell membranes is the introduction of a cyclohexyl group. If the cyclohexyl group is part of the ring component, due to the relatively more hydrophobic nature, incorporation into a membrane may be favored, but the susceptibility of the Si—O—C bonds to hydrolysis is maintained. In a variation, a cyclohexyl group substituted onto the silicon atom provides additional hydrophobicity, but the steric substitution slows hydrolysis.

The silacrown ethers according to embodiments of the disclosure have many therapeutic applications, such as playing an important role in mitigating vasoconstriction, and therefore have beneficial effects in CHF. The underlying chemistry of crown ethers may allow for specific targeting of system versus pulmonary vascular smooth muscle which may allow for providing beneficial effects in these diseases. Additionally, the unique structure of the inventive compounds may allow them to permeabilize the cell membrane, thereby allowing chemotherapeutic drugs to enter the cell.

Accordingly, the disclosure also relates to a method of treating a disease selected from the group consisting of CVD, cancer, bacterial infections, parasites, and any disease associated with modulation of ion transport channels, the method comprising administering to a subject in need thereof a silacrown ether comprising at least fourteen ring atoms, one methyl group on the silicon atom, and at least one lipophilic or hydrophobic substituent on the silicon atom and/or on the ring, provided that if the at least one lipophilic or hydrophobic substituent is a methyl group on the silicon atom, the silacrown ether further comprises at least one lipophilic or hydrophilic substituent on the ring. Appropriate hydrophobic substituents are as previously described.

The disclosure further relates to a method of treating a disease selected from the group consisting of CVD, cancer, bacterial infections, parasites, and any disease associated with modulation of ion transport channels, the method comprising administering to a subject in need thereof a silacrown ether comprising at least seventeen ring atoms, at least one methyl group on the silicon atom, and at least one lipophilic or hydrophobic substituent on the silicon atom and/or on the ring.

The invention will now be described in connection with the following, non-limiting examples.

Example 1: Synthesis of Dimethylsila-14-cyclohexylcrown-5

Under a $N_2$ atmosphere, a 1-Liter-4-neck flask equipped with a cooling bath, overhead stirrer, pot thermometer, addition funnel, and dry ice condenser was charged with hexane (9.75 mole, 840 g), dimethyldichlorosilane (0.65 mole, 83.9 g), and triethylamine (1.33 mole, 134.8 g). The mixture was cooled to 0° C. and 2-[2-[2-(2-hydroxyethoxy)ethoxy]ethoxy]-cyclohexanol (0.65 mole, 161.4 g) was add via addition funnel between 0° C. and 10° C. over an hour. After the addition was completed, the mixture was warmed to 20° C. to 30° C. and stirred one extra hour. The mixture was filtered through a Buchner funnel and washed with 200 ml hexane twice. The organic solvent was removed under vacuum. Product was cracked at 350° C. at 0.1 mmHg to give 21.2 g of desired product (Yield: 15%), $^1$H NMR (400 MHz, $CDCl_3$) δ 0.117 (m, 6H), 1.184 (m, 4H), 1.292 (m, 1H), 1.612 (m, 2H), 1.850 (m, 1H), 1.954 (m, 1H), 3.5-3.7

(m, 11H), 3.799 (t, 2H). FTIR ν(Si—O): 1085 cm$^{-1}$. B.p. 120-125° C./0.1, density@20° C.: 1.059 g/ml/

Example 2: Synthesis of Cyclohexylmethylsila-14-crown-5

Under a N$_2$ atmosphere, a 1-Liter-4-neck flask equipped with a heating mantle, overhead stirrer, pot thermometer, addition funnel, and packed column with distillation head was charged with tetraethylene glycol (2 moles, 388.5 g), cyclohexylmethydimethoxysilane (2.5 moles, 470.9 g), and 0.5 ml titanium n-butoxide. The mixture was heated to 100° C. to 120° C. while controlling head temperature between 62~68° C. for 10 hours. The next day, the pot was heated to 200° C. while keeping the distillation head <90° C. Once reaching 200° C., product was stripped from 760 to 0.2 mmHg to give 627.7 g crude product. The crude product was then redistilled at 150° C./0.2 mmHg to give 357.2 g of desired product (56% yield). $^1$H NMR (400 MHz, CDCl$_3$) δ 0.065 (s, 3H), 0.777 (m, 1H), 1.151 (m, 5H), 1.688 (m, 5H), 3.652 (m, 12H), 3.857 (m, 4H). FTIR ν(Si—O): 1096.63 cm$^{-1}$. B.p. 150° C./0.2, density@20° C.: 1.075 g/ml.

Example 3: Oral Toxicity Studies

An acute oral toxicity study in adult albino Sprague-Dawley rats in compliance with Good Laboratory Practice was performed and the acute oral LD50 for three compounds was determined to be greater than 5000 mg/kg: dimethylsila-14-crown-5: 9,900 mg/kg; dimethylsila-17-crown-6: >5000 mg/kg; and dimethylsila-14-cyclohexylcrown-5: >5000 mg/kg. No mortality was observed during the study. Animals exhibited weekly weight gain during the studies. Animals were asymptomatic by day 3. Gross necroscopy conducted at terminal sacrifice revealed no observable abnormalities. These data can be compared with the LD50 acute oral toxicity in mice for crown ethers which have been reported by Gad et al. as: 12-crown-4: 2830 mg/kg; 15-crown-5: 2100 mg/kg; 18-crown-6: 1590 mg/kg. Further, the dicyclohexano-crown ethers have been reported with significantly greater toxicity: dicyclohexano-18-crown-6: 176 mg/kg and dicyclohexano-24-crown-8: 75 mg/kg. Thus, crown ethers and silacrown ethers of similar cavity size behave similarly, but the silacrown ethers have dramatically lower toxicity.

Example 4: Investigation of Vascular Tissue Contractile Response as a Function of Crown and Silacrown Ether Concentration Under the guidance of Dr. Keith Pannell (University of Texas) and Dr. Robert A.

Ginsburg (Stanford University Medical School), crown and silacrown ethers in concentrations of 10$^{-8}$M, 10$^{-7}$ M, 10$^{-6}$ M and 10$^{-5}$M were prepared fresh daily in deionized water. The 10$^{-5}$ M concentrations were used for the preliminary screening of the ionophores for vasoactivity to determine the most promising candidates. The procedures utilized in the removal and preparation of vascular smooth muscle tissue obtained from aorta of white New Zealand rabbits and human hearts from transplant patients are well established and have been successfully utilized by the personnel at Stanford University Medical School (Cardiology Department). A computer interfaced muscle bath system designed by Dr. Robert Ginsburg and associates was used to carry out the experimental procedure. The chambers (32 per system) were filled with standard Tyrode solution (chambers maintain a constant volume of 100 ml) and aerated continuously. The tissues were placed in the chambers and connected to stainless steel hooks to a linear motion transducer and preequilibrated for 1.5 hours at a constant temperature of 37° C. (a tension of 0.5 g was maintained during the pre-equilibration period).

A starting tension of approximately 0.5 g was achieved before adding the agonist (40 nM KCl final concentration) to contract the tissues. After the contractions leveled off, the tensions were recorded before and after the crown ethers were added. To test for tissue integrity, 10$^{-5}$ M nitroglycerin was added at the end of the experiment (some relaxation should be observed), and the tension was recorded.

Due to the limited amount of time and availability of human tissue, the crown ethers were preliminarily screened at a concentration of 10$^{-5}$ M using the vascular smooth muscle tissue obtained from rabbits. Four to six chambers were used per ionophore. Approximately four to six chambers were used for controls. Only the most promising ionophores were selected and studied.

Accumulative dose response curves were obtained by repeating the previous procedure on both human and rabbit vascular smooth muscle tissues as previously described. However, crown ether concentrations of 10$^{-8}$ M, 10$^{-7}$ M, 10$^{-6}$ M and 10$^{-5}$ M were added accumulatively instead of only one dose (10$^{-5}$ M was used to screen the crowns) and the tensions recorded for each concentration (before the next concentration of ionophore was added, the contractile tension of the tissue had leveled off). The reduction of original contraction (relaxation) can be observed from the data obtained at each concentration and displayed in FIG. 1 for crown ethers versus silacrowns and for crown ethers with cyclohexyl and benzenoid ring substituents (15-crown-5, cyclohexano-15-crown-5, and benzo-15-crown-5) in FIG. 2.

Figure 1:
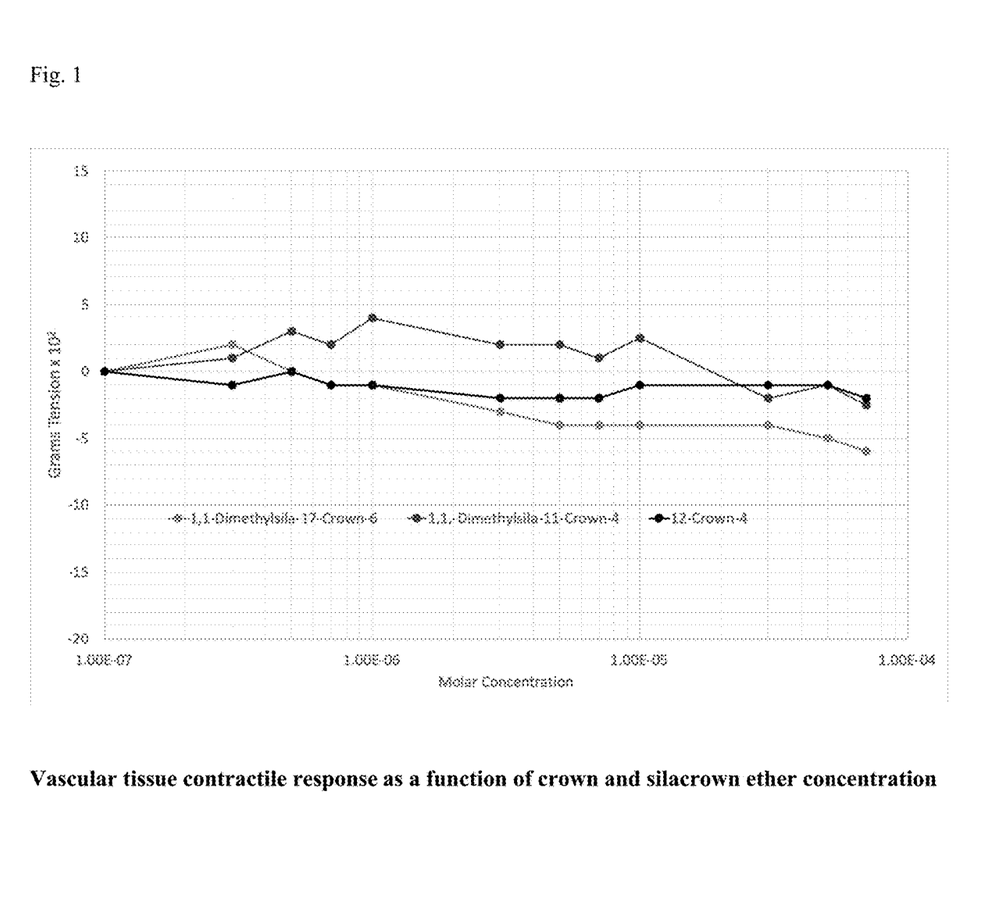
FIG. 1 is a graph of vascular tissue contractile response as a function of crown and silacrown ether concentration based on the data in Example 4.
Figure 2:
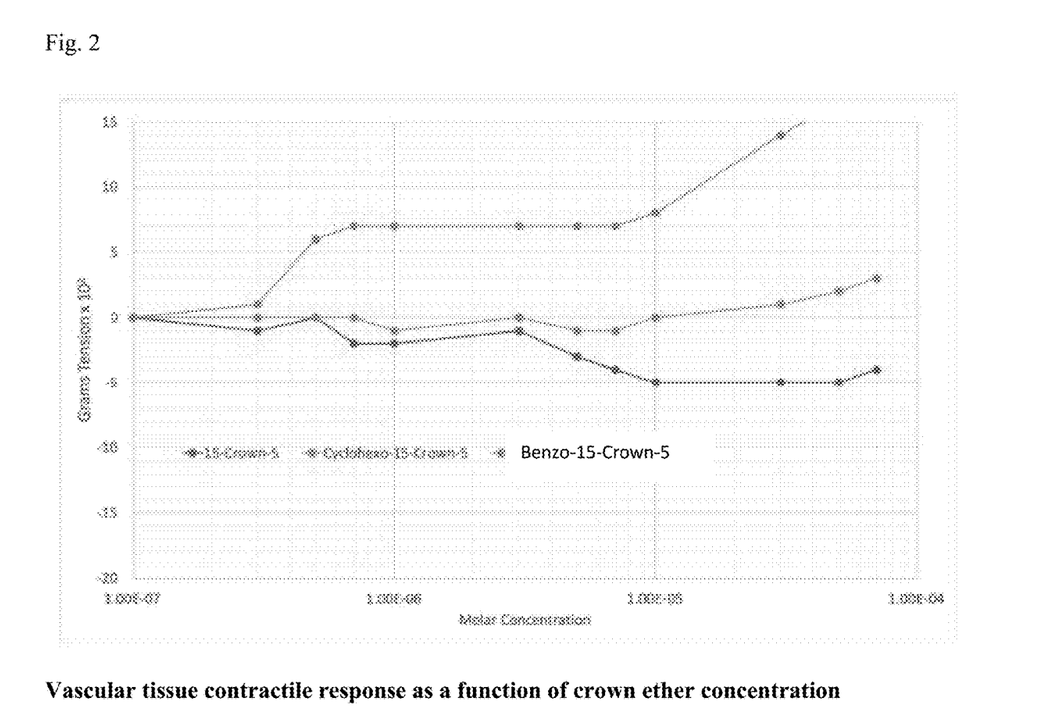
FIG. 2 is a graph of vascular tissue contractile response as a function of various crown ethers as a function of concentration based on the data in Example 4.

It may seen in FIG. 1 that the contractile response of vascular smooth muscle tissue at various concentrations of 12-crown-6, 1,1-dimethylsila-17-crown-6, and 1,1-dimethylsila-11-crown-4 was similar. However, neither class had a profound effect on vascular tissue behavior. Further, as shown in FIG. 2, the non-silicon-containing crown ethers become physiologically active when there is a cyclohexyl or phenyl group present. However, they are not acceptable for therapeutic use due to their high toxicity. Additional experimental data for crown ethers showed greater relaxation trends when the ring size was 18 members or greater, with a maximum observed when the ring members were 24 or greater and two cyclohexyl ring components were present.

These data clearly demonstrate that the silacrown ethers provide similar advantages to known materials with reduced toxicity.

Example 5 (Prophetic): Vascular Tissue Contractile Response of Dimethylsila-cyclohexano-23-crown-8

Dimethylsila-cyclohexano-23-crown-8 is prepared in a method analogous to that described in Example 1. When administered to rabbit aortic tissues as described in Example 4 at a concentration of $10^{-6}$M, the tissue will demonstrate strong relaxation properties and the sila-crown-ether will be a promising therapeutic agent for treating a wide variety of diseases of the vasculature including systemic hypertension, pulmonary hypertension and vasospasm. Additionally, the ability to alter cellular permeability in a targeted fashion is highly promising as an adjunctive agent for chemotherapy and antibiotic applications.

It will be appreciated by those skilled in the art that changes could be made to the embodiment described above without departing from the broad inventive concepts thereof. Also, based on this disclosure, a person of ordinary skill in the art would further recognize that the relative proportions of the components illustrated above could be varied without departing from the spirit and scope of the invention. It is understood, therefore, that this invention is not limited to that particular embodiment disclosed, but it is intended to cover modifications within the spirit and scope of the present invention as defined by the appended claims.

We claim:

1. A silacrown ether having fourteen to twenty-three non-aromatic ring atoms of which one of the ring atoms is silicon, two methyl groups on the silicon ring atom, at least one linear, branched, or cyclic alkyl group substituent having one to twenty-four carbon atoms on a non-silicon non-aromatic ring atom, and optionally at least one benzene group on a non-silicon ring atom.

2. The silacrown ether according to claim 1, wherein the silacrown ether has at least one cyclohexane group on a non-silicon ring atom.

3. The silacrown ether according to claim 1, wherein the silacrown ether has at least one benzene group on a non-silicon ring atom.

4. The silacrown ether according to claim 1, wherein the silacrown ether is a sila-dicyclohexano-23-crown-8 or a sila-cyclohexano-23-crown-8.

5. The silacrown ether according to claim 1, wherein the silacrown ether is dimethylsila-14-cyclohexyl-crown-5.

6. The silacrown ether according to claim 1, wherein the silacrown ether is a sila-dicyclohexano-14-crown-5.

7. A therapeutic agent comprising a silacrown ether according to claim 1.

8. A pharmaceutical composition comprising a pharmaceutically acceptable carrier and a silacrown ether according to claim 1.

9. A method of treating a disease selected from the group consisting of cardiovascular disease and muscular tissue disorders, the method comprising administering to a subject in need thereof a silacrown ether according to claim 1.

10. A silacrown ether having fourteen to twenty-three ring atoms of which one of the ring atoms is silicon, one methyl group on the silicon ring atom, at least one linear, branched, or cyclic alkyl group substituent having three to twenty-four carbon atoms on the silicon ring atom and/or on a non-silicon ring atom, and optionally at least one benzene group on a non-silicon ring atom.

11. The silacrown ether according to claim 10, wherein the silacrown ether has at least one cyclohexane group on the silicon ring atom and/or on a non-silicon ring atom.

12. The silacrown ether according to claim 10, wherein the silacrown ether has at least one benzene group on a non-silicon ring atom.

13. The silacrown ether according to claim 10, wherein the silacrown ether is a sila-dicyclohexano-23-crown-8 or a sila-cyclohexano-23-crown-8.

14. The silacrown ether according to claim 10, wherein the silacrown ether is cyclohexylmethylsila-17-crown-6.

15. The silacrown ether according to claim 10, wherein the silacrown ether is cyclohexylmethylsila-20-crown-7.

16. The silacrown ether according to claim 10, wherein the silacrown ether is a sila-dicyclohexano-14-crown-5.

17. The silacrown ether according to claim 10, wherein the silacrown ether is cyclohexylmethylsila-14-crown-5.

18. A therapeutic agent comprising a silacrown ether according to claim 10.

19. A pharmaceutical composition comprising a pharmaceutically acceptable carrier and a silacrown ether according to claim 10.

20. A method of treating a disease selected from the group consisting of cardiovascular disease and muscular tissue disorders, the method comprising administering to a subject in need thereof a silacrown ether according to claim 10.

21. A method of treating a disease associated with modulation of ion transport channels associated with contractile response of cardiovascular tissue, the method comprising administering to a subject in need thereof a silacrown ether according to claim 1.

22. A method of treating a disease associated with modulation of ion transport channels associated with contractile response of cardiovascular tissue, the method comprising administering to a subject in need thereof a silacrown ether according to claim 10.

* * * * *